United States Patent [19]
Kwan-Gett

[11] Patent Number: 5,151,105
[45] Date of Patent: Sep. 29, 1992

[54] COLLAPSIBLE VESSEL SLEEVE IMPLANT

[76] Inventor: Clifford Kwan-Gett, 3017 St. Mary's Cir., Salt Lake City, Utah 84124

[21] Appl. No.: 772,067

[22] Filed: Oct. 7, 1991

[51] Int. Cl.$^5$ .............................................. A61F 2/06
[52] U.S. Cl. .................................. 623/1; 606/153; 606/191; 604/96; 604/264; 604/280
[58] Field of Search ................................ 604/93–96, 604/280–282, 264; 606/151, 153, 191, 192; 623/1, 10

[56] References Cited

U.S. PATENT DOCUMENTS

| | | | |
|---|---|---|---|
| 3,710,399 | 1/1973 | Hurst | 623/10 |
| 4,778,466 | 10/1988 | Brotman | 623/10 |
| 4,820,298 | 4/1989 | Leveen et al. | 623/10 |

FOREIGN PATENT DOCUMENTS

2494581  5/1982  France .

*Primary Examiner*—David Isabella
*Assistant Examiner*—Gina M. Gualtieri
*Attorney, Agent, or Firm*—M. Reid Russell

[57] ABSTRACT

An implantable collapsible tubular sleeve for implanting inside a live tissue fluid vessel and system, the sleeve ends each including a collapsible circular stent or annular balloon affixed thereto. A pair of linear stiffeners are each attached to opposite sleeve exterior sides, in longitudinal orientation, and the sleeve is adapted to be collapsed and maintained in that collapsed state to be fed along the patients's femoral artery and into position within an abdominal or throacic aorta, spanning an aortic aneurysm. A capsule band is wound around to maintain the collapsed sleeve for travel to the aneurysm, and it is maneuvered through the femoral artery on a guide wire by means of a catheter. At the aneurysm the capsule band is removed and the sleeve released, forming its cylindrical configuration. The circular stents or annular balloons at the sleeve ends can be adjusted to be perpendicular to the aorta axis and are urged into the graft wall into sealing engagement with the aorta lumen. After positioning, sleeve implant may be stabilized utilizing a tacking system operated from within the graft, to drive barbed ends of tacks through the sleeve inner wall and into the artery wall. The tacking system is operated by pulling an erecting ball between flexing arms, the arms pivoting outwardly to drive barbed ended tack releasably mounted thereto through the sleeve to lodge in the aorta wall, which barbed end tacks are then released from the flexing arms.

29 Claims, 3 Drawing Sheets

COLLAPSIBLE VESSEL SLEEVE IMPLANT

BACKGROUND OF THE INVENTION

1. Field of the Invention

This invention relates to surgically implantable sleeves for implanting inside of blood vessels, and more particularly relates to such a sleeve that is collapsible such that it can be implanted in the aorta or other artery through an incision or percutaneous puncture into the lumen of the femoral artery.

1. Prior Art

This invention was set out and described in an earlier U.S. patent application, Ser. No. 07/201,191, now abandoned.

Stable and asymptomatic abdominal aortic aneurysms are quite common. The standard treatment for asymptomatic abdominal aortic aneurysms is to surgically remove the aneurysm and graft a replacement prosthetic section into the aorta. However, such surgery is generally postponed until the aneurysm has grown to a diameter greater than five cm. With aneurysms over five cm in diameter, the risk of complications is greater than the risks inherent in surgical excision and grafting of the aneurysm. Consequently, symptomatic aortic aneurysms, or those that show a rapid increase in size, or those greater than five cm in diameter are generally surgically removed and grafted as a matter of course, before rupture occurs.

The standard surgical procedure for repairing an abdominal aneurysm includes one or two days of preparing the large and small intestines prior to hospitalization. The actual operation generally takes one to three hours, and may necessitate four or more units of blood transfusion. The patient commonly remains hospitalized for seven to ten days following surgery, and usually requires as much as three months recuperation time before returning to work.

Even for this elective surgical excision and grafting of an abdominal aortic aneurysm, there remains significantly high rates of mortality and morbidity. The mortality rate is as high as five percent (5%). The morbidity rate includes incident complications such as blood loss, respiratory tract infections, wound infections, graft infections, renal failure, and ischemia of the bleeding intestine. The mortality and morbidity rates for this type of major surgery are also often influenced by the fact that the typical aortic aneurysm patient is elderly and therefore less able to withstand major surgery and a major anesthetic.

The common surgical procedure for repairing an abdominal aortic aneurysm is to excise part or all of the aneurysm and replace the aneurysmal aortic section with a man made tubular section, sutured end-to-end to the severed aorta at a site proximal to the origination of the aneurysm. Other types of replacement sections have flat metal rings or tube sections in each end. These metal rings or tube sections are placed inside the exposed aorta ends, and retained in place by either securing ligatures around the exposed ends to compress the aorta against the metal tube sections, or by clamping the exposed aorta ends against the tube sections with a metal or other suitable clamp.

Other non-aneurysmal medical treatments have involved positioning various devices in place via a catheter into the vascular system. The intra-aortic balloon pump is almost always placed in position via the femoral artery. Such an arrangement is shown in a Kreamer U.S. Pat. No. 4,577,631. The balloon pump is only a temporary device, however, and must be surgically removed within days or weeks.

A device known as a Mobin-Uddin umbrella is a stainless steel and silicone rubber device that is used to trap thromboembolic traveling along the inferior vena cava towards the heart and lungs. This device is generally placed in position within the inferior vena cava via the internal jugular vein, or via the femoral vein.

Similarly, a filter known as a stainless steel Greenfield filter can be placed in position with a catheter into the inferior vena cava, via the femoral vein or the internal jugular vein.

Further, several conduit prosthesis for implantation as a surgical treatment for dissecting an aortic aneurysm are shown in Whalen U.S. Pat. No. 4,130,904 and Koyamada U.S. Pat. No. 4,313,231. Also, grafts, similar to the present invention in that they are characterized as being movable from a collapsed formation of a diameter less than the diameter of a vessel to an open formation of a diameter approximately equal to that of a vessel, are shown in Choudhury U.S. Pat. No. 4,140,126 and to Kornberg, No. 4,562,596, none of which collapsible grafts alone or in a reasonable combination, however, anticipate the present invention, as set out and claimed herein.

As set out above, it is well known to place devices within the vascular system via catheters. Conventional tubular aortic replacement sections, however, are generally considerably larger in diameter than the femoral artery and therefore cannot be inserted through the femoral artery lumen. Also, where such devices have been proposed, for example the devices of the Choudhury and Kornberg patents, the expanding structure thereof appears to be cumbersome, difficult to operate, is generally unreliable and is structurally different from the present invention. Additionally, even if it were possible to position such a tubular aortic section within the aortic aneurysm, prior to the tacking device set out herein, it was essentially impossible, without major surgery, to secure ligatures or other clamps around the aorta to compress so as to secure the aorta against the tubular aortic section.

SUMMARY OF THE INVENTION

Objects of the Invention

It is an object of the present invention to provide an implantable vessel sleeve that is collapsible to a very small diameter in order that it may be placed in position within the abdominal or thoracic aorta by a catheter and positioning wires via the lumen of the femoral artery.

It is a parallel object of the present invention to provide an implantable vessel sleeve that does not require major abdominal surgery on the abdominal aorta in order to effect implantation.

It is another object of the present invention to provide an implantable vessel sleeve that expands from a collapsed state to fluid seal against an aortic interior wall.

It is still another object to provide an implantable vessel sleeve that will maintain itself in a stable position after placement in a patient.

It is still another object of the present invention to additionally provide a device for stabilizing the seated implantable vessel that is operated from within the vessel sleeve for driving barbed ended pins, through the sleeve and aortic walls, locking the vessel sleeve in place.

An ultimate objective of the present invention is to drastically reduce the rates of mortality and morbidity associated with the surgical treatment of stable and ruptured abdominal aortic aneurysms.

Features of the Invention

These and other objects and advantages are obtained by a vessel sleeve implant of the present invention dimensioned to, when in expanded in sealing engagement against the interior wall of a "normal" aorta. The vessel sleeve implant is situated across a ruptured or non-ruptured abdominal aortic aneurysm, thereby isolating the flow of blood from the aneurysm and removing the high blood pressure from the wall of the aneurysm. The vessel sleeve implant, as disclosed, is collapsible down to approximately twenty-five percent of its expanded diameter (and therefore down to approximately six percent of its expanded cross-sectional area) in order that it may be fed into the vascular system, and specifically into the abdominal aorta, via the femoral artery. The sleeve is cylindrical in shape and is constructed of a suitable synthetic fabric, such as "Dacron". With each end of the sleeve fitted with an end stent comprising a circular spring designed to expand radially outwardly, while maintaining a generally circular shape. So arranged, the ends of the sleeve implant are uniformally urged against the interior wall of the vessel in order to immediately provide a fluid tight seal with the wall.

The sleeve implant vessel also includes a pair of longitudinal ribs or stiffeners, positioned in the cylindrical wall to extend longitudinally and to be spaced 180 degrees from each other on the sleeve (i.e., on diametrically opposite sides of the cylindrical sleeve). These longitudinal ribs or stiffeners provide a length adjustment capability to and structure to the sleeve and further assist in dividing the drag resistance force of moving fluid through the sleeve between the spaced apart circular spring stents, each of which are frictionally attached to the vessel interior wall.

A spiral capsule band is provided in which the collapsible sleeve is encapsulated during introduction into the vascular system. The sleeve and capsule are connected to a catheter and two positioning wires which enable the encapsulated sleeve to be maneuvered within the vascular system so as to be positioned within the aortic aneurysm. A guide wire within the catheter then functions to release the collapsed sleeve from the spiral capsule band and to release the capsule band, so that the positioning wires can be used to precisely adjust the expanding sleeve into position across the aneurysm.

After which vessel sleeve setting and its expansion, to maintain a permanent seating, a remotely operated tacking device is moved through the vascular system and into the expanded vessel sleeve implant. A covering sleeve is then pulled off from the tacking device that is operated to drive barb ends of tacks into the sleeve and aortic wall. The barbs to penetrate the aortic wall and prevent tack withdrawal, locking the sleeve in place. Which tack head ends are released from the tacking device that is then withdrawn from the vascular system.

While the apparatus of the present invention is preferably designed for abdominal aortic aneurysms, it may also be used for thoracic aortic aneurysms, and aortic dissections or other sites of leakage from the arteries or veins.

Other objects and features of the invention will become apparent from the following detailed description and drawings disclosing what is presently contemplated as being the best mode of the invention.

DETAILED DESCRIPTION OF THE INVENTION

Figure 7:
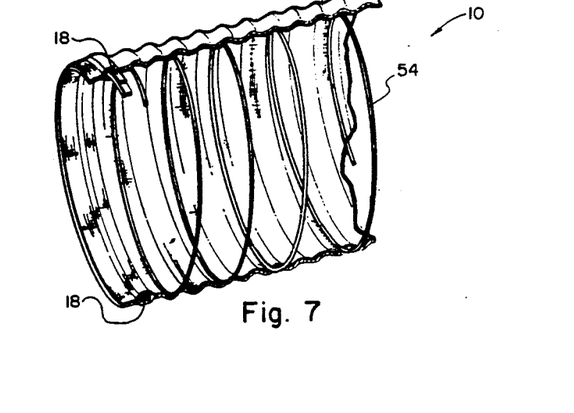
FIG. 7, is a sectional view similar to FIG. 2, but showing an optional spring wire for retaining the sleeve implant against the interior wall of the vessel.
Figures 8, 9A:
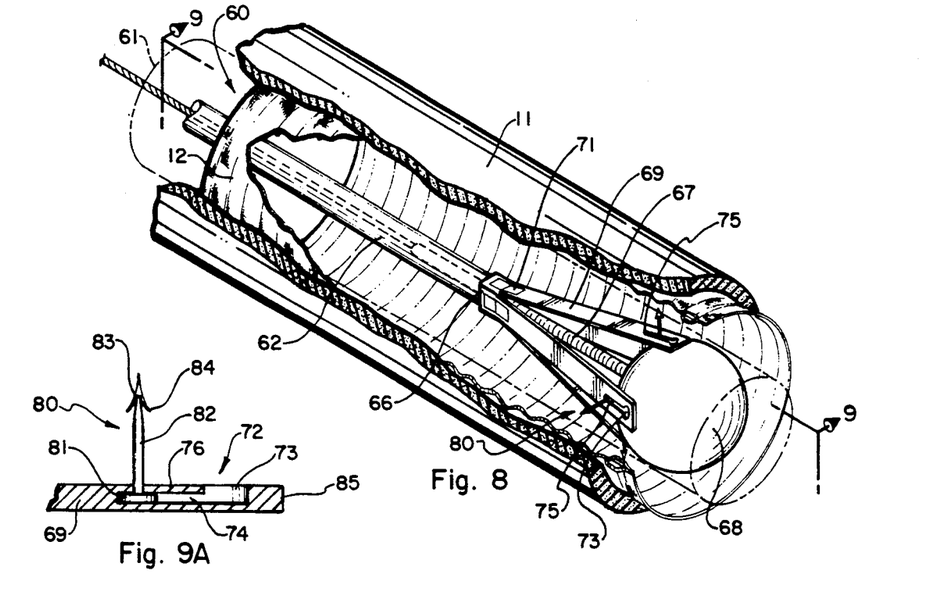
FIG. 8 is a perspective view of a tacking system of the present invention shown as having been positioned within the sleeve implant and is partially erected within that sleeve implant.
FIG. 9A is an expanded sectional view taken within the line 9A—9A of FIG. 9, showing a barbed ended flat head tack of the tacking system mounted in a retaining slot of a tacking system flexing arm.
Figure 9:
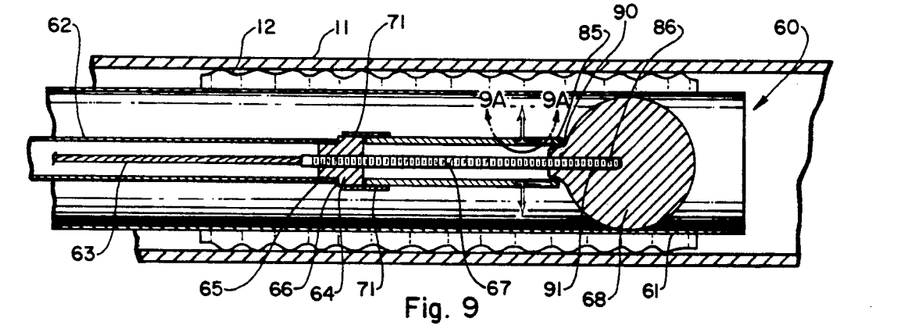
FIG. 9 is a sectional view taken along the line 9—9 of FIG. 8 showing the tacking system contained within a covering sleeve and installed in the sleeve implant with an erecting ball of that tacking system mounted onto an end of a pull rod, the erecting ball shown at its forward most point of travel.
Figure 10:
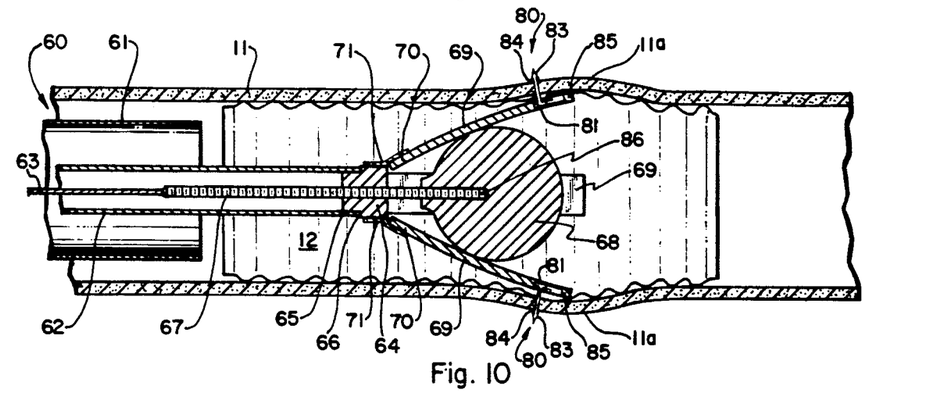
FIG. 10 is a view like FIG. 9 only showing the covering sleeve pulled off the tacking system, with the erecting ball shown pulled between the flexing arms, extending which flexing arms outwardly, the barbed ends of tacks shown passed through the sleeve and vessel wall.

Referring now to the drawings:

The collapsible vessel implant 10, shown in FIGS. 1 through 7 of the present invention, is for installation as a arterial graft, as shown in FIGS. 8 through 10. Sleeve implants have been used in the medical industry and are commonly referred to as grafts and therefore the present invention will be hereinafter referred to as a graft.

The graft 10 as shown, for installation in an artery 11, shown as a healthy artery in FIGS. 8, 9 and 10, through, of course, for the intended procedure such artery would have an aneurysm, or like defect, to be repaired utilizing graft 10. The graft 10 comprises a generally cylindrical or tubular body portion 12 that is open at each end. The graft body portion is constructed as a cylindrical sleeve of a material capable of becoming substantially liquid impermeable, such as "Dacron" fabric, manufactured by DuPont. As illustrated, the graft body portion 12 is formed as a sleeve bellows so that the graft 10 may easily be compressed or elongated slightly, while retaining its generally cylindrical configuration.

For purposes of convention, the left end as shown in the drawings, will be designated the leading open end 14, and the right end will be designated the trailing open end 16.

Figure 1:
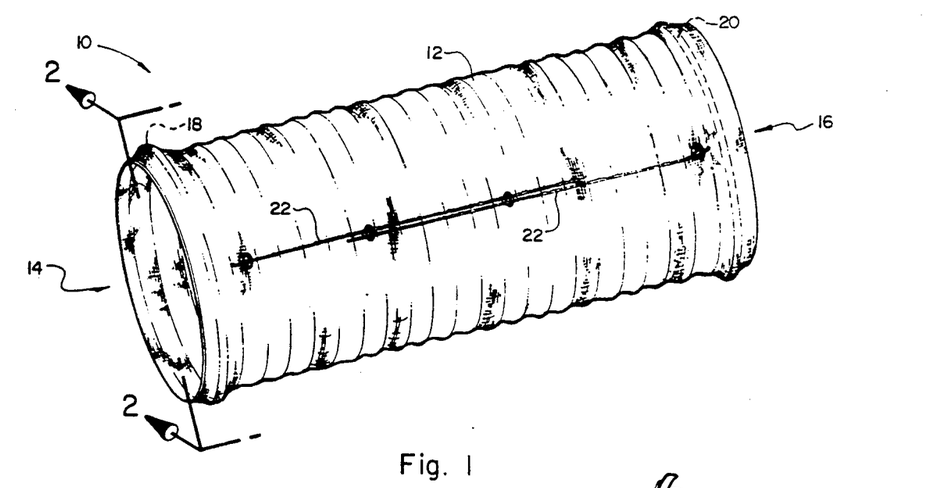
FIG. 1 is a perspective view of the collapsible sleeve implant of the present invention in its fully expanded condition.
Figure 2:
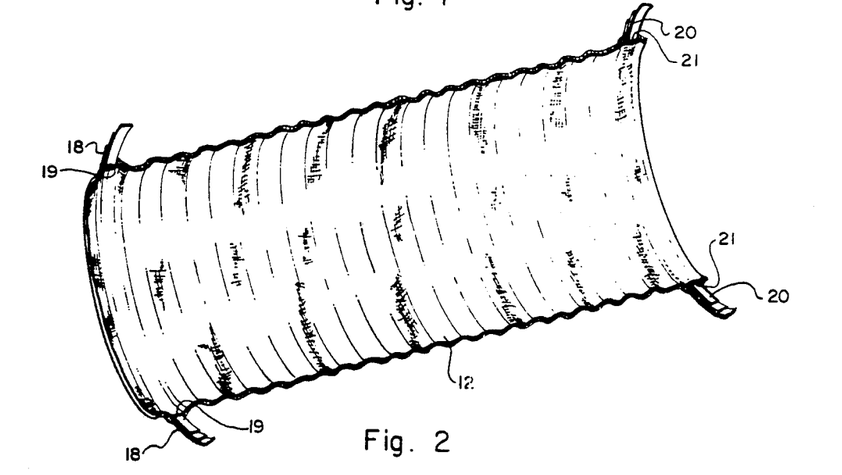
FIG. 2, is a sectional view of the collapsible sleeve implant, taken along lines 2—2 of FIG. 1.

The open ends 14 and 16 have generally circular leading end and trailing end stiffening members 18 and 20 formed therein, respectively, as shown best in FIG. 2. These stiffening members are commonly designated as circular stents and therefore will be so referred to herein. The circular stents 18 and 20 may be sutured to the interior wall of the body portion 12, adjacent the respective open ends 14 and 16, or, as shown in the drawings, each may be placed inside annular pockets 19 and 21, respectively, that are located adjacent the respective body portion open ends. Also as shown best in FIG. 2.

In the preferred embodiment, shown in FIGS. 1 through 4, the circular stents 18 and 20 preferably comprise lengths of thin, flat spring material (stainless spring steel, in this instance) that are concentrically wound into torsion springs, similar to a watch or clock spring. In this embodiment, three or four turns of the wound spring are sufficient. The inventor has determined that such a concentrically wound spring design provides the necessary collapsibility to be described hereinbelow), while also providing the uniform radially outward expansion of the ends of the graft 10, necessary to effect a tight seal of the graft against the interior wall of the vessel under repair.

Referring again to FIG. 1, the graft body portion 12 includes a pair of longitudinal stiffeners 22 for preventing central collapse of the body portion 12 and thus maintaining the body portion extended to is desired longitudinal dimension. The longitudinal stiffeners 22 are constructed of resilient spring steel or similar material that will retain its shape following temporary slight elastic distortion, such as would be encountered when positioning the graft with a major blood vessel. As shown in the drawings, the longitudinal stiffeners 22 are positioned to extend axially (longitudinally) along the exterior cylindrical wall of the graft body portion 12 for providing a length adjustment capability to and for stiffening the cylindrical wall, and are sutured or otherwise loosely attached to the exterior wall in a manner to permit adjustability of the overall length of the graft 10. Although depicted in the drawings as being a single pair of stiffeners positioned adjacent each other on the graft exterior wall, it will be understood that preferably two such pairs of longitudinal stiffeners 22 may be used, as the pairs, each stiffener of a pair being positioned one hundred eighty degrees (180°) apart from one another, i.e., diametrically opposed from each other. In either configuration, as will be further explained, the longitudinal stiffeners permit precise adjustment of the overall length of the graft 10, and will bridge a damaged vessel section while maintaining such precise length adjustment across an area where an aneurysm exists, in a living vascular system.

Figure 3:
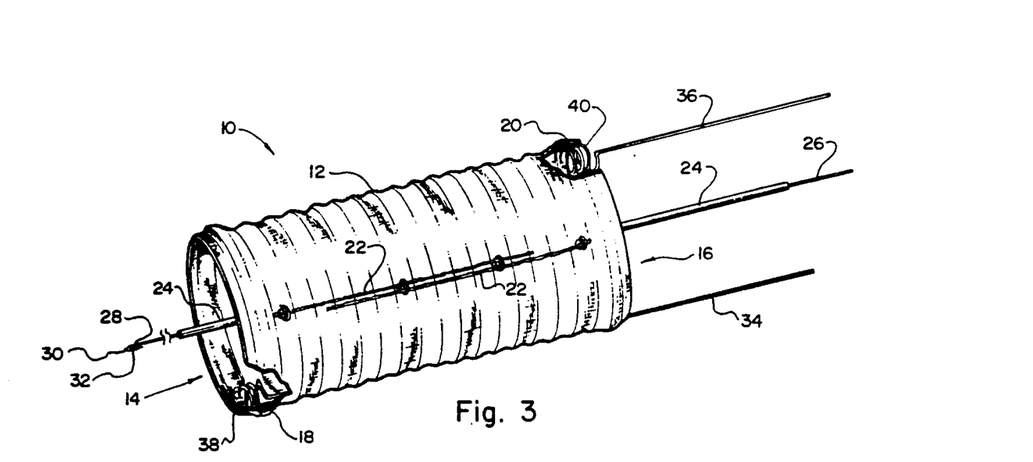
FIG. 3, is a perspective view similar to FIG. 1, also illustrating the guide wire and positioning wires.
Figure 4:
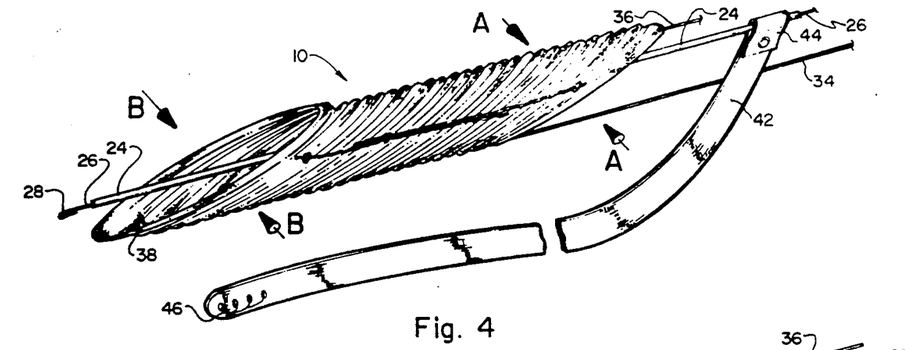
FIG. 4, is a perspective view of the sleeve implant shown in mid-collapsed form prior to spiral wrapping with a spiral capsule band.
Figures 5, 6:
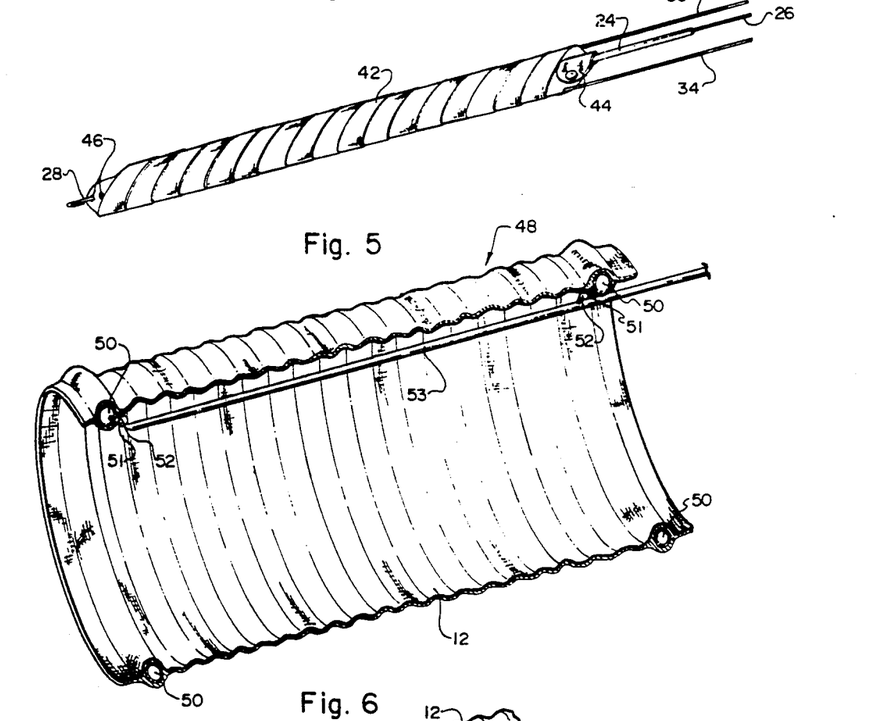
FIG. 5, is a perspective view of the sleeve implant, shown in collapsed form and encapsulated within the spiral capsule band.
FIG. 6, is a sectional view similar to FIG. 2, but showing an alternative means for sealing the sleeve against the vessel interior wall, taking the form of inflatable annular balloons.

As best shown in FIG. 4 and 5, the collapsible graft 10 of the present invention is intended to be inserted into a stable and/or ruptured aortic aneurysm via an incision or puncture in the vascular system, which puncture is at a location somewhat remote from the aneurysm, for instance the femoral artery. To accomplish this the graft 10 is adapted to be removably attached to the end of a catheter 24 and guide wire 26 shown also in FIG. 3. The guide wire 26 is slidably positioned within the catheter 24 in a manner to be freely slidable within that catheter, (and therefore within the graft 10) even when the graft 10 is collapsed, as described hereinbelow. The guide wire 26 preferably is of conventional construction and may include a reversely turned end 28 into a wide hook, to prevent tissue damage as the wire is inserted.

Shown best in FIG. 3, the graft 10 is also adapted to be removably attached to first and second positioning wires 34 and 36. Which positioning wires 34 and 36 include respective spiral or corkscrew-type ends 38 and 40. As shown in FIG. 3, the first corkscrew end 38 of the first positioning wire 34 is adapted to attach to the graft 10 adjacent the leading open end 14 and leading circular stent 18. Similarly, the second corkscrew end 40 of the second positioning wire 36 is adapted to attach to the graft adjacent the trailing open end 16 and trailing circular stent 20. It will be apparent that the ends 38 and 40 could alternatively be attached by twisting into the body portion 12.

As shown, the positioning wires 34 and 36 are diametrically opposed from one another about an axis along the geometric longitudinal center of the cylindrical body portion 12 and are oriented to be outstanding from the longitudinal stiffeners 22. As will be described in greater detail hereinbelow, this particular orientation of the first and second positioning wires 34 and 36 assist in feeding the graft into the vascular system and also in the precise positioning of that graft within a normal aorta length and across an aneurysm or other damaged area of that aorta. Additionally, the positioning wires may be graduated or length marked in order to permit the surgeon to precisely position the graft where desired, by noting the distance that the graft has been fed into the femoral artery incision, or, of course, the installation may be practiced by a surgeon viewing a fluoroscopic monitor, within the scope of this disclosure.

The implantable sleeve or graft 10 of the present invention is intended to be collapsible down to approximately twenty-five percent, or less, of its expanded diameter (and therefore down to approximately six percent of its expanded cross-sectional area). Shown in FIG. 4, this collapsibility is accomplished by (1) initially skewing the tubular graft toward its trailing end, and (2) compressing the circular stents 18 and 20, shown in FIG. 2, inwardly toward the catheter 24 at the locations adjacent the end points of connection of the longitudinal stiffeners 22 to the tubular body portion 12, as shown by arrows A and B in FIG. 4. As shown, the first and second positioning wires 34 and 36 are twisted onto and thus removably attached to opposite circular stents 18 and 20 at diametrically opposed points of attachment about the cylindrical body portion 12. The graft 10 is then skewed beyond the position shown in FIG. 4, to the point of being essentially flat against the catheter 24. For purposes of illustration, however, the graft is shown in only a partially flattened orientation in FIG. 4.

The next step in collapsing the graft 10 of the present invention is a further compression of the graft body and the circular stents 18 and 20. This is preferably accomplished manually by initially squeezing the trailing circular stent 20 in the direction of arrows A and B. With the trailing circular stent 20 sufficiently compressed, a capsule band 42 is spirally wrapped around the collapsed and compressed graft 10 from the point of attachment 44 to the catheter toward the leading end of the graft 10. This capsule band 42 is preferably made of polyurethane or similar material that is very thin, strong and slippery so that it will facilitate easy movement of the graft within the vascular system. As the capsule band 42 is wrapped around the graft, the leading circular stent 18 is manually squeezed in the direction of arrows A and B, so as to totally collapse the graft. With the leading end of the graft so collapsed, the capsule band 42 is tightly spirally wrapped around the remaining exposed graft, and that band is then fastened by positioning an end hole 46 in the band over the guide wire hooked end 28. This connection provides for retaining the capsule band 42 tightly spirally wrapped around the graft 10. This tightly collapsed and bound graft and capsule band are then ready for introduction into the vascular system, for positioning across an aortic aneurysm, for instance.

FIG. 6, shows an alternative embodiment 48 of the collapsible graft of the present invention. In this embodiment, the circular stents have been replaced with inflatable annular balloons 50 at each end of the graft 20 body portion. Each of these balloons includes an inlet tube 51 having a check valve 52 therein. Each inlet tube is connected to a small diameter air or fluid supply tube 53, in turn, that extends alongside guide wire 26.

Installation of this alternative embodiment 48 is basically similar to that of the previously described embodiment. Accordingly, the graft 48 is initially skewed and collapsed, as described in relation to the previous graft 10 embodiment, and the capsule band 42 is tightly spirally wound and anchored around the graft.

Following positioning of the collapsed graft within the aorta, across an aneurysm, according to the procedure previously described, the capsule band is removed and withdrawn. Removal of the capsule band 42 from around the graft 48 of FIG. 6, however, does not in this instance, cause the annular balloons 50 to automatically expand to their natural circular shape as with the circular stents 18 and 20 of graft 10. Rather, the surgeon must inflate the annular balloons through a tube 53 fitted into the vascular system that has a nozzle end 52 that coupled into inlet tubes 51, on inflation, the balloons 50, form circular stents that function in the same manner as the previously described coiled spring stents 18 and 20. Inflation of the balloons 50 expands outer surface of the graft 40 radially outwardly to seal against the interior surface of the aorta 11, or other blood vessel.

FIG. 7, illustrates still another embodiment graft 10 of the invention. As shown, a coiled wire spring 54 that is positioned inside the graft 10 to prevent collapse of any section of the graft body portion 12. The ends of the coiled wire spring 54 abut ridges that are adjacent to and are formed by the circular stents 18 and 20, in the graft interior wall, or they may be anchored to the circular stents themselves. In either anchoring configuration, the coiled wire spring 54 functions to urge the graft body portion radially outwardly against the blood vessel interior wall to improve the fluid seal between the graft and the vessel wall and to prevent the possibility of collapse of the graft.

The above described graft 10 and 48 configurations are arranged for erecting the tubular body portion 12 in an artery 11, or other part of a patient's vascular system, to cover over a damaged or injured wall section, the tubular body portion to seal thereacross providing a free flow path therethrough. While the described grafts 10 and 48 provide for sealing against the aortic wall, that seal, or time, may not prevent graft movement along that wall as could displace it from its covering attitude over an aneurysm, or like damaged area of an aorta. For positively prohibiting graft displacement, the present invention, as shown in FIGS. 8 through 10, provides a tacking system, wherewith a surgeon can, fit a tacking system 60 into the vascular system to a position within the graft tubular body portion 12. Whereat, a covering sleeve 61 is pulled off from the tacking system, as shown in FIG. 10.

The tacking system 60, shown in FIGS. 8 through 10, is for arrangement on the end of a catheter 62 containing a sliding guide wire 63. The catheter is capped by a mount 64 that is necked in at 65 for fitting in the catheter end, engaging a mount wall 66 contacted by that catheter end. The mount 64 is axially center holed to receive a draw rod 67 slidably fitted therein, which draw rod connects, on a trailing end, to the guide wire end 63 and is secured to an erecting ball 68 on its opposite, or leading end. Equidistantly spaced flexing arms 69 are pivotally secured at their trailing ends to leading portions of flexing tabs 71. The trailing portions of which flexing tabs 71 are individually secured to the mount 64 leading end surface, each forming a pivot coupling.

The flexing arms 69, as shown in FIGS. 8 and 9A, are arranged in pairs each flexing arm positioned one hundred eighty degrees (180°) apart from the other, each including a keyway track formed thereon that includes a large diameter port 73 that dog legs longitudinally, shown at 74, within the flexing arm, with a narrow slot 75 provided between shoulders 76 at the flexing arm surface. Shown best in FIG. 9A, the large diameter passage 73 is for receiving a head 81 end of a barbed tack 80 fitted therein, the tack body 82 to travel freely along the slot 75, the head traveling within the dog leg 74, to a stowed attitude. Shown best in FIG. 9A, the barbed tack 80 includes a pointed barb end 83 that, as set out below, is to penetrate and travel through the graft body portion 12 and aorta 11, to extend slightly beyond the aorta outer wall, as shown in FIG. 10. The tack body 82 length is selected to provide for travel of the base 84 of the tack pointed barb end 83 to travel just beyond the aorta outer surface, that base flexing outwardly to bind into the aorta surface, prohibiting withdrawal. The tack 80 is installed, as shown in FIG. 10, permanently tacking the graft 10 in place within the aorta.

Shown best in FIGS. 9 and 10, the erecting ball 68 includes a cylindrical collar 90 formed on its spherical surface with a center hole 91 formed through that collar and to the erecting ball 68 center. The cylindrical collar 90 has a diameter that allows it to fit between the leading ends 85 of the flexing arms 69. The center hold 91, as shown in FIGS. 9 and 10, is tapped or otherwise formed to receive a threaded end 86 of the draw rod 67 that is turned therein to the end hole 91, for permanent locking of the draw rod to the erecting ball.

With the catheter 62 held stationary, a covering sleeve 61 is pulled off of the tacking system 60 and with the erecting ball 68 secured to the draw rod 67, by pulling the guide wire 63 and connected draw rod, as shown in FIG. 10, the erecting ball 68 is pulled between the ends 85 of the flexing arms 69. The undersurfaces of which flexing arm ends 85 slide and pivot outwardly along the erecting ball 68 surface, as shown in FIG. 8, to where the flexing arms 69 are fully spread apart, as shown in FIG. 10. In which attitude, the tack barbed ends will have been forced through the sleeve and aorta walls. Each barb end barb 84 is to engage and bind into the aorta outer surface, prohibiting tack 80 withdrawal.

Thereafter, to release the individual seated tacks 80 from the flexing arms 69 tension on the guide wire 63 is relaxed and urged oppositely causing the draw rod 67 and erecting ball 68 to move towards the graft 10 leading edge. A bulge 11a, shown in FIG. 10, is thereby relaxed and pressure on each of the tack heads 81 head undersurface is relaxed, allowing it to slide along the surface of the longitudinal dog legs 74. Thereafter, by applying a controlled tension on the catheter 62 to move the tacking system 60, the barbed tacks 80 head ends 81 will travel along the surfaces of the dog legs 74 to where which head ends 81 align with the lateral passage 73. Whereat, by fully releasing tension on the guide wire 63 and, as necessary, applying a compressive force thereto, the erecting ball 68 will travel back to the attitude shown in FIG. 9. In which attitude, the seated barb tacks head ends 81 will be freed to pass out of the large diameter port 73 as the flexing arms 69 are flexed inwardly. With further flexing arm inward flexing, the tack head ends 81 pass out of the ports 73, leaving the barbed tacks 80 seated in the sleeve 10 and aorta 11, tacking the graft 10 onto the aorta lumen to prevent movement of the graft within the aorta. Whereafter the covering sleeve 61 is slid back over the tacking system, as shown in FIG. 9, and the assembly is removed.

As set out above, the barbed tack body 82 length and barbed end 83 configuration thereof is selected to draw the tack head 81 undersurface into a close fitting sealed engagement with the graft body portion 12 inner surface, prohibiting a blood flow around said barbed tack head end, which head 81 thickness is preferable narrow to reduce a chance of blood clot formation thereat. In practice, any blood flow reaching the tack body 82 would be slight.

The graft 10 is secured with barbed tacks 80, as described above, at intervals along the sleeve, as a surgeon determines. With the above described sealing action of the sleeve head ends to the aorta lumen a safe permanent grafting mounting is provided for redirecting a blood flow across a damaged section of aortic wall. The diameter of the artery proximal to the aneurysm is determined by X-ray, CAT scan or ultrasound and then an appropriately sized collapsed vessel sleeve implant is chosen. The expanded diameter of the implant is chosen to be slightly greater than the internal diameter of the artery, and a length is selected to move then cover the length of the aneurysm.

PROCEDURE

As set out above, the collapsible vessel sleeve implant or graft 10 of the present invention is intended to be implanted and stabilized inside a normal aorta section to bridge a ruptured or stable aortic aneurysm. This is accomplished by introducing the collapsed graft into the patient's vascular system, and maneuvering it inside that vascular system into a position inside the aorta and spanning the aneurysm, where it is expanded and is held in place by the inflating of barbed tacks 80. The procedure for accomplishing this includes initially attaching the first and second positioning wires 34 and 36 to the graft at the ends adjacent the leading and trailing circular stents 18 and 20, respectively. Secondly, the catheter 24 and guide wire 26 are positioned axially inside the graft, as depicted in FIG. 3. Next, the graft 10 is collapsed and tightly spirally wrapped in the capsule band 42, as described. The guide wire end 28 is inserted into the aorta and is positioned in conventional manner as surgically practiced.

The collapsed and bound graft is then inserted into the vascular system over the prepositioned guide wire through an incision or puncture in the femoral artery. As the circular stents, longitudinal stiffeners and tacking system components are preferably radiopaque, the surgeon will be able, by fluoroscopy, to monitor the movement of the graft through the vascular system and can precisely position it and tack, with barbed tacks, the graft into position within the aorta across a aneurysm or like damaged portion. Additionally, the positioning wires may be graduated to permit accurate measurement of the distance the graft has traveled in the vascular system, for aiding the surgeon in precisely positioning the graft.

Once the collapsed graft 10 is in approximate position within the aorta and aneurysm, the surgeon removes the spiral capsule band permitting the graft to spring towards its expanded normal tubular configuration, and makes the adjustments necessary to precisely position and anchor the graft 10. The spiral capsule band is then released by withdrawing the guide wire 26, thereby freeing the capsule band end containing hole 46 to allow the capsule band to uncoil itself from around the graft.

The graft, released by removal of the wound capsule band, springs towards its natural tubular shape as the circular stents expand towards their normal circular configuration. With the graft partially expanded from its collapsed configuration, the catheter and guide wire may be withdrawn from the vascular system. As the catheter is withdrawn it pulls the capsule band from the vascular system.

At this point, the graft is normally still partially collapsed or skewed, similar to the orientation shown in FIG. 4, and requires further manipulation in order to precisely position and fully expand the graft within the aorta and aneurysm. This is accomplished by use of the two positioning wires 34 and 36, which are still attached to the leading and trailing ends of the graft body portion. It should be apparent that by pulling on the leading positioning wire 34 while simultaneously pushing on the trailing positioning wire 36, the surgeon can complete the positioning of the graft within the aorta and its aneurysm. Additionally, the surgeon can rotate the graft slightly, both as he feeds it through the vascular system toward the aneurysm, and also as he precisely positions the graft at the location of the aneurysm. This is accomplished by rotating or "torquing" both positioning wires as a set as he urges the wires into the vascular system, or as he reciprocates the graft into precise position once it is initially positioned within the aorta and aneurysm.

With a proper graft size selected and that graft located in a proper position within the aorta, across the aneurysm, the surgeon may then slightly agitate or reciprocate the positioning wires to make the circular stents adopt positions in planes normal to the axis of the aorta. This dilates the aorta slightly around the circular stents at opposite end of the aneurysm to provide a more positive friction sealed adherence to the aorta interior wall.

The graft 48 embodiment of FIG. 6 is similarly installed with a release of the capsule band 42. Whereafter, the annular balloon ends 50 are inflated as described, sealing against the aorta interior wall. The annular balloon stents of this embodiment, like the circular stents 18 and 20, will also embed in any grumous or soft material present on the interior wall of the aorta.

After the graft 10 is in the desired position within the aorta and aneurysm, the surgeon detaches the positioning wires from the graft. This is accomplished by rotating the positioning wires individually, in order to "unscrew" the corkscrew positioning wire attachments 38 and 40 from their respective points of attachment to the circular stents. Once removed from the graft, the positioning wires can be withdrawn from the patient's body. With a femoral artery percutaneous puncture, hand pressure on the puncture site may be sufficient to allow the puncture site to seal.

After graft 10 seating and removal of the positioning wires through the femoral artery incision, for permanently maintaining graft position, the tacking system 60 is inserted into the vessel system to a position within the body portion 12. The covering sleeve 61 is then pulled from its covering arrangement, and the barbed tacks 80 mounted to the flexing arm ends are aligned with points around the aorta lumen deemed to be suitable for supporting the tack barb ends, which selected points are preferably on both sides of the aneurysm, though tacking of one graft side on the up stream side may provide sufficient holding strength. The tacking system is then operated, as described above, to drive the tacks 80 through the graft and aorta, the barb ends lodging in the aorta outer surface material, securing the tacks and permanently fixing the graft in place. The tacking system 60 is then withdrawn, and, as necessary, reloaded with barbed tacks and repositioned to drive the barbed tacks into the graft and aorta around the opposite body portion 12 end, on the graft spanning the aneurysm. The seated barb tacks prohibit movement of the graft within the aorta as could uncover the aneurysm, or damaged area.

While four (4) equidistantly spaced flexing arms 69 are shown, as preferred, it should be understood that as few as two (2) such flexing arms, equidistantly spaced, could be utilized and operated, as described within the scope of this disclosure. After which barbed tack installation the tacking system including the covering sleeve is pulled therefrom and the femoral artery incision is repaired, as set out above.

In some patients, the lumen of the aorta may be quite firmly irregular or eccentric, so that the stented ends of the graft do not form a tight seal with the intima of the aorta even after installation, as described of the barbed tacks. In the grafting of a stable aneurysm, however, this should not prevent the use of the stented graft, since the diminished blood flow around the outside of the graft should result in sufficient stasis to cause eventual clotting of the space between the graft and the dilated intima. If after a period of several days, an angiogram shows that the extraliminal space has not clotted off, then the patient may still have a standard surgical procedure for excision of the aneurysm and its contained graft and replacement with an artificial aortic graft in the presently known usual manner.

Although preferred forms of my invention have been shown and described herein, it is to be understood that the present disclosure is made by way of example and that variations are possible without departing from the subject matter coming within the scope of the following claims and a reasonable equivalency thereof, which subject matter I regard as my invention.

I claim:

1. An implantable collapsible tubular sleeve for implanting inside a live tissue fluid vessel, said sleeve comprising an open-ended generally cylindrical body portion being flexible and collapsible, a pair of resilient and substantially circular stiffening members positioned and integral with said sleeve at opposite annular ends of said body, a pair of longitudinal stiffening members extending parallel to a central axis of said sleeve, each member having one end attached to a body portion of the sleeve and opposite ends overlapping and loosely extending from a middle portion of said body for adjusting the length of said sleeve, and means for positioning and erecting said sleeve in said live tissue fluid vessel.

2. A collapsible vessel sleeve according to claim 1, wherein said body portion is constructed of a synthetic fabric material.

3. A collapsible vessel sleeve according to claim 1, further including a coil spring positioned inside of said sleeve for urging said body portion against the interior wall of said live tissue fluid vessel.

4. A collapsible vessel sleeve according to claim 1, wherein each of said resilient, essentially circular stiffening members comprises at least one spring coil formed of a flat spring steel material.

5. A collapsible vessel sleeve according to claim 4, wherein the flat spring steel material for forming the spring coil, is a plurality of overlapping, essentially concentric windings, arranged as a plurality of leafs.

6. A collapsible vessel sleeve according to claim 1, wherein each of said resilient, essentially circular stiffening members comprises an inflatable annular balloon.

7. A collapsible vessel sleeve according to claim 1, wherein the means for positioning and erecting includes a removable encapsulating means for encapsulating the sleeve to permit said sleeve to be inserted into and through said live tissue fluid vessel.

8. A collapsible vessel sleeve according to claim 7, further including catheter means attached to the sleeve for inserting said sleeve into and maneuvering it through said live tissue fluid vessel.

9. A collapsible vessel sleeve according to claim 8, further including a pair of positioning wires removably attached to the sleeve for precisely positioning said sleeve within said live tissue fluid vessel.

10. A system for maintaining an implantable collapsible tubular sleeve inside a live tissue fluid vessel comprising, a tacking system for mounting on an end of a catheter wherein a draw wire is fitted to slide longitudinally within said catheter; a draw rod and connected erecting means, said erecting means having a curved surface outwardly from its connection to said draw rod mounted to an end of said draw wire; at least a pair of flexing arm means that are individually pivotally mounted on one end of said catheter end that is positioned within an implantable collapsible tubular sleeve having means for maintaining longitudinal stiffening of said sleeve, said means extending parallel to said sleeve central longitudinal axis to receive said erecting means curved surface between which flexing arms, with each flexing arm releasably maintaining a tack means extending outwardly from its opposite end; a tack means having a broad head on one end of a straight shaft with a pointed barbed end as the other shaft end; and means for releasably maintaining said tack, pointed barbed end pointing outwardly from each said flexing arm means.

11. A collapsible vessel sleeve according to claim 10, wherein the erecting means is a sphere having a cylindrical collar extending from its surface, said cylinder to fit between the flexing arm ends and receives the draw rod secured thereto.

12. A collapsible vessel sleeve according to claim 10, wherein the flexing arms pivotal coupling is a flexible tab connected along one edge to said flexing arm end and to a catheter end mount along its opposite edge.

13. A collapsible vessel sleeve according to claim 10, wherein the tack shaft length is selected to provide for the tack barbed end passing through which implantable collapsible tubular sleeve and lodging in the wall of the live tissue fluid vessel to provide a snug fit of the tack head undersurface against said implantable collapsible tubular sleeve interior surface.

14. A collapsible vessel sleeve according to claim 10, wherein the means for releasably maintaining the tack to the flexing arm means is a lateral opening into said flexing arm means to freely pass the tack head end therein; a right angle longitudinal passage in said flexing arm means to intersect said lateral opening, with spaced apart flanges above said longitudinal passage that with a longitudinal space therebetween to accommodate the tack shaft sliding therebetween.

15. A collapsible vessel sleeve according to claim 10, further including a covering sleeve means for travel with the catheter, covering the tacking system, that is arranged to be slide by an operator out of covering engagement over said tacking system positioned within the implantable collapsible tubular sleeve.

16. An implantable collapsible sleeve system comprising a sleeve, for implanting inside a live tissue fluid vessel, having an open-ended, generally cylindrical body portion being flexible and collapsible, and a pair of resilient and substantially circular stiffening members positioned and fixed to opposite annular ends of said sleeve; a guide wire extending through said body portion; a catheter positioned to slide on said guide wire through the interior of said cylindrical body portion a flexible wrapping having one end fixed to said catheter adjacent said one end of the body portion and an opposite end of said flexible wrapping fixed to said guide wire adjacent said opposite end of said body portion, said flexible wrapping mounted to slide over said guide wire and spirally wrapping around said body portion before being fixed to said opposite end of said body portion, and means for maintaining said sleeve at a site within a live tissue vessel.

17. A collapsible vessel sleeve according to claim 16, further including at least one longitudinal stiffening member extending substantially the length of the body portion; and means for securing each said longitudinal stiffening member to said body portion such that said longitudinal stiffening member extends substantially parallel to the central axis of said body portion and said body portion is movable axially with respect to the longitudinal stiffening member.

18. A collapsible vessel sleeve according to claim 17, further including a pair of positioning wires each having one end releasably attached to one of the opposite ends of the body portion and extending substantially parallel to the catheter.

19. A collapsible vessel sleeve according to claim 18, wherein the ends of the positioning wires attached to the ends of the body portion are formed as spirals that are screwed into said body portion and that are removed by screwing them out of said body portion.

20. A collapsible vessel sleeve according to claim 19, wherein the annular stiffening members are constructed of spring steel.

21. A collapsible vessel according to claim 20, wherein the annular stiffening members include a plurality of annular windings.

22. A collapsible vessel sleeve according to claim 20, wherein the annular stiffening members are inflatable bands.

23. A collapsible vessel sleeve according to claim 16, wherein the flexible wrapping is made of a strong sheet material having a smooth exterior surface.

24. An implantable collapsible vessel sleeve system according to claim 16, wherein the means for maintaining the sleeve at a site within the live tissue fluid vessel is a tacking system for mounting on an end of a catheter wherein a draw wire is fitted to slide longitudinally; a draw rod and connected erecting means, said erecting means having a curved surface outwardly from its connection to said draw rod mounted to an end of said draw wire; at least a pair of flexing arm means that are individually pivotally mounted on one end of said catheter end that is positioned within said sleeve to receive said erecting means curved surface between which flexing arms, with each said flexing arm releasably maintaining a tack means extending outwardly from its opposite end; a tack means that is a tack having a broad head on one end of a straight shaft with a pointed barbed end as the other shaft end; and means for releasably maintaining said tack, pointed barbed end, pointing outwardly from each said flexing arm means.

25. An implantable collapsible vessel sleeve system according to claim 24, wherein the erecting means is a sphere having a cylindrical collar extending from its surface, said cylinder to fit between the flexing arm ends and receives the draw rod secured thereto.

26. An implantable collapsible vessel sleeve system according to claim 24, wherein the flexing arms pivotal coupling is a flexible tab connected along one edge to said flexing arm end and to a catheter end mount along its opposite edge.

27. An implantable collapsible vessel sleeve system according to claim 24, wherein the tack shaft length is selected to provide for the tack barbed end passing through which sleeve and lodging in the wall of the live tissue fluid vessel to provide a snug fit of the tack head undersurface against said sleeve interior surface.

28. An implantable collapsible vessel sleeve system according to claim 24, wherein the means for releasably maintaining the tack to the flexing arm means is a lateral opening into said flexing arm means to freely pass the tack head end therein; a right angle longitudinal passage in said flexing arm means to intersect said lateral opening, with spaced apart flanges above said longitudinal passage and with a longitudinal space therebetween to accommodate the tack shaft sliding therebetween.

29. An implantable collapsible vessel sleeve system according to claim 24, further including a covering sleeve means for travel with the catheter, covering the tacking system, that is arranged to be slid by an operator out of covering engagement over said tacking system positioned within the sleeve.

* * * * *